United States Patent
Zhang

(10) Patent No.: US 7,330,761 B2
(45) Date of Patent: Feb. 12, 2008

(54) BASELINE ADAPTATION FOR CARDIAC PACING RESPONSE CLASSIFICATION

(75) Inventor: Geng Zhang, Newbury Park, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 376 days.

(21) Appl. No.: 11/012,608

(22) Filed: Dec. 15, 2004

(65) Prior Publication Data

US 2006/0129198 A1    Jun. 15, 2006

(51) Int. Cl.
*A61N 1/362*    (2006.01)
(52) U.S. Cl. .......................... 607/28; 600/521
(58) Field of Classification Search ................. 607/13, 607/28; 600/509, 521
See application file for complete search history.

(56) References Cited

U.S. PATENT DOCUMENTS

| | | |
|---|---|---|
| 5,374,280 A | 12/1994 | Den Dulk |
| 5,458,623 A | 10/1995 | Lu et al. |
| 5,476,482 A | 12/1995 | Lu |
| 5,871,509 A | 2/1999 | Norén |
| 6,408,210 B1 | 6/2002 | Bornzin et al. |
| 6,456,881 B1 | 9/2002 | Bornzin et al. |
| 6,473,649 B1 * | 10/2002 | Gryzwa et al. ............... 607/28 |
| 6,498,949 B2 | 12/2002 | Levine et al. |
| 6,697,673 B1 | 2/2004 | Lu |
| 6,950,704 B1 * | 9/2005 | Bradley ...................... 607/28 |

\* cited by examiner

*Primary Examiner*—Kennedy J. Schaetzle
(74) *Attorney, Agent, or Firm*—Hollingsworth & Funk, LLC

(57) ABSTRACT

Methods and devices for establishing and using baseline for cardiac pacing response detection are described. A baseline amplitude of the cardiac signal may be established using data acquired in an evaluation interval prior to the delivery of the pacing pulse. An amplitude of the cardiac signal following delivery of the pacing pulse may be referenced using the baseline amplitude. An evoked response from the pacing pulse is detected using the referenced cardiac signal amplitude.

15 Claims, 6 Drawing Sheets

BASELINE ADAPTATION FOR CARDIAC PACING RESPONSE CLASSIFICATION

RELATED PATENT DOCUMENT

This patent application is related to commonly owned U.S. patent application Ser. No. 11/012,430 filed concurrently herewith Dec. 15, 2004 and incorporated herein by reference.

FIELD OF THE INVENTION

The present invention relates generally to implantable medical devices and, more particularly, to initializing and adapting baselines and/or templates for evoked response detection following delivery of a pace pulse.

BACKGROUND OF THE INVENTION

When functioning normally, the heart produces rhythmic contractions and is capable of efficiently pumping blood throughout the body. However, due to disease or injury, the heart rhythm may become irregular resulting in diminished pumping efficiency.

Arrhythmia is a general term used to describe heart rhythm irregularities arising from a variety of physical conditions and disease processes. Cardiac rhythm management systems, such as implantable pacemakers and cardiac defibrillators, have been used as an effective treatment for patients with serious arrhythmias. These systems typically include circuitry to sense electrical signals from the heart and a pulse generator for delivering electrical stimulation pulses to the heart. Leads extending into the patient's heart are connected to electrodes that contact the myocardium for sensing the heart's electrical signals and for delivering stimulation pulses to the heart in accordance with various therapies.

Cardiac rhythm management systems operate to stimulate the heart tissue adjacent to the electrodes to produce a contraction of the tissue. Pacemakers are cardiac rhythm management systems that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

When a pace pulse produces a contraction in the heart tissue, the electrical cardiac signal following the contraction is denoted the captured response (CR). The captured response may include an electrical signal, denoted the evoked response (ER) signal, associated with the heart contraction, along with a superimposed signal associated with residual post pace polarization at the electrode-tissue interface. The magnitude of the residual post pace polarization signal, or pacing artifact, may be affected by a variety of factors including lead polarization, after-potential from the pace pulse, lead impedance, patient impedance, pace pulse width, and pace pulse amplitude, for example.

A pace pulse must exceed a minimum energy value, or capture threshold, to produce a contraction. It is desirable for a pace pulse to have sufficient energy to stimulate capture of the heart without expending energy significantly in excess of the capture threshold. Thus, accurate determination of the capture threshold is required for efficient pace energy management. If the pace pulse energy is too low, the pace pulses may not reliably produce a contractile response in the heart and may result in ineffective pacing. If the pace pulse energy is too high, the patient may experience discomfort and the battery life of the device will be shorter.

Capture detection allows the cardiac rhythm management system to adjust the energy level of pace pulses to correspond to the optimum energy expenditure that reliably produces a contraction. Further, capture detection allows the cardiac rhythm management system to initiate a back-up pulse at a higher energy level whenever a pace pulse does not produce a contraction.

At times, a pacing pulse may merge with an intrinsic beat, producing a fusion beat. A fusion beat is a cardiac contraction that occurs when two cardiac depolarizations of a particular chamber, but from separate initiation sites, merge. When the heart is being paced, a fusion beat may occur when an intrinsic cardiac depolarization of a particular chamber merges with a pacemaker output pulse within that chamber. Fusion beats, as seen on electrocardiographic recordings, exhibit various morphologies. The merging depolarizations of a fusion beat do not contribute evenly to the total depolarization.

Pseudofusion occurs when a pacemaker output pulse is superimposed upon a spontaneous P wave during atrial pacing or upon a spontaneous QRS complex during ventricular pacing. In pseudofusion, the pacing stimulus may be ineffective because the tissue around the electrode has already spontaneously depolarized and is in its refractory period.

During normal pacing, the presence of fusion or pseudofusion beats may be of little consequence except for wasted energy due to the generation of unnecessary pace pulses. However, detection of fusion or pseudofusion beats may be desired during an automatic capture or threshold determination procedure. Fusion or pseudofusion beats may cause false detection of capture and may lead to erroneous capture threshold values.

SUMMARY OF THE INVENTION

The present invention involves various methods and devices for adapting baselines for evoked response detection from pacing stimulation. Embodiments of medical systems in accordance with the present invention include a cardiac therapy system configured to deliver a cardiac therapy to a patient and a sensing system configured to sense cardiac waveforms. A processor is coupled to the sensing system and the cardiac therapy system, the processor configured to deliver a pacing pulse to a heart chamber, sense a cardiac signal from the heart, establish a baseline amplitude of the cardiac signal using data acquired in an interval prior to the delivery of the pacing pulse, and detect an evoked response from the pacing pulse using the baseline amplitude. The processor may be configured to average the data within the interval, and may further include a voltage hold circuit useful as a baseline amplitude reference.

Other methods of adapting a baseline for characterizing a cardiac response to pacing in accordance with the present invention involve delivering a pacing pulse to a heart chamber and sensing a cardiac signal from the heart. A baseline amplitude of the cardiac signal is established using data acquired in an interval prior to the delivery of the pacing pulse. An evoked response from the pacing pulse is detected using the baseline. The pacing pulse to the heart chamber may be delivered to one or more of the right or left atrium and the right or left ventricle.

The baseline amplitude for the cardiac signal may be established using data acquired in an interval having a range of about 3 msec to about 10 msec, and may include an averaging mask. For example, the averaging mask may have an output level coupled to a voltage holder, the voltage holder used as the baseline amplitude reference.

The above summary of the present invention is not intended to describe each embodiment or every implementation of the present invention. Advantages and attainments, together with a more complete understanding of the invention, will become apparent and appreciated by referring to the following detailed description and claims in conjunction with the accompanying drawings.

Figure 1:
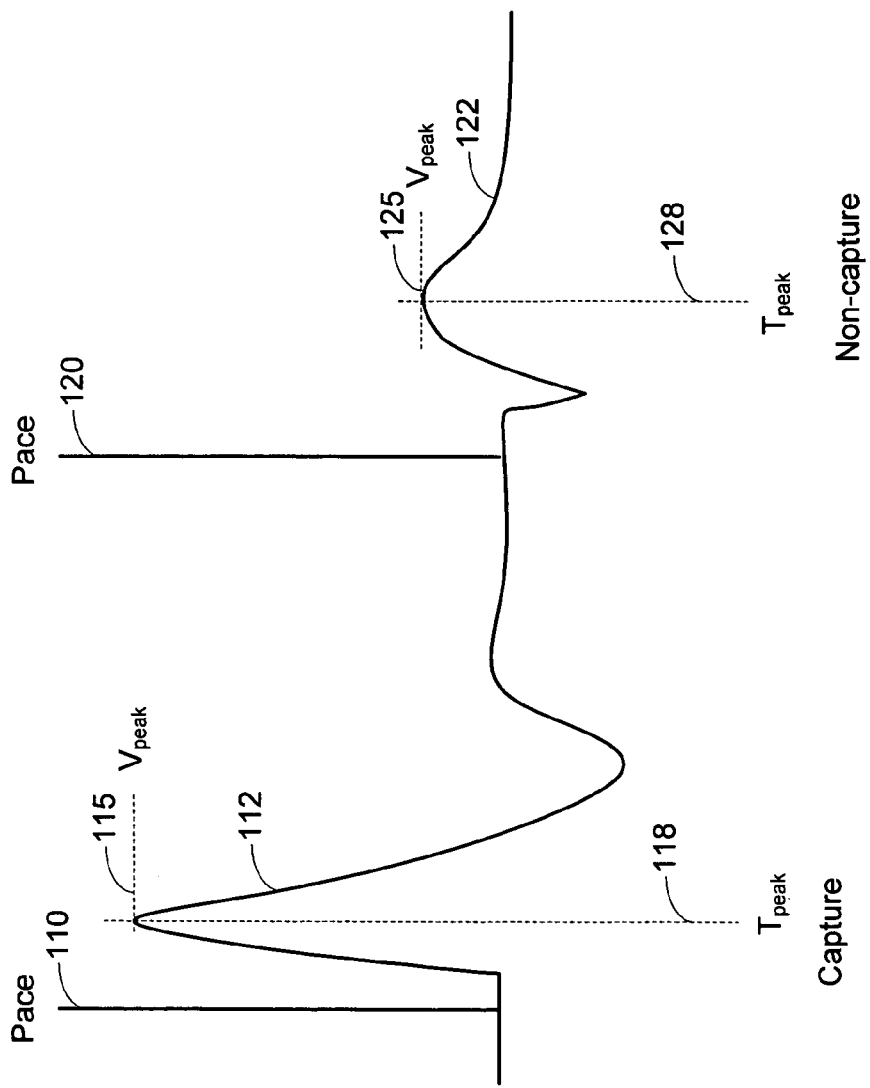
FIG. 1 is a graph illustrating two consecutive heartbeats including a captured response and a non-captured response.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown, by way of illustration, various embodiments by which the invention may be practiced. It is to be understood that other embodiments may be utilized, and structural and functional changes may be made without departing from the scope of the present invention.

Cardiac rhythm management (CRM) devices such as pacemakers operate to stimulate the heart tissue via implanted electrodes to produce a contraction of the tissue. A series of low energy pace pulses may be delivered to the heart, the pacing pulses timed to assist the heart in producing a contractile rhythm that maintains cardiac pumping efficiency. Pacing may be intermittent or continuous, depending on the needs of the patient. There exist a number of categories of pacemaker devices, with various modes for sensing and pacing one or more heart chambers.

After delivery of a pacing pulse to a heart chamber, various cardiac responses to the pacing pulse are possible. In one scenario, the pacing pulse may generate a propagating wavefront of depolarization resulting in a contraction of the heart chamber. In this scenario, the pacing pulse is said to have captured the heart chamber. Capture of the heart chamber may occur if the pacing pulse has sufficient energy and is delivered during a non-refractory period. If the pacing pulse does not produce contraction of the chamber, the cardiac response is referred to as non-capture. Non-capture may occur, for example, if the pacing pulse energy is too low, and/or if the pacing pulse is delivered during a refractory period of the cardiac tissue. In another scenario, an intrinsic depolarization wavefront may merge with a depolarization wavefront produced by the pacing pulse. The merged intrinsic and paced beats are referred to as a fusion beat.

The minimum pacing energy that produces capture is referred to as the capture threshold. It is desirable for a pace pulse to have sufficient energy to capture the heart without expending excess energy above the capture threshold. Thus, accurate determination of the capture threshold is desirable for efficient pacing.

Capture threshold determination is distinguishable from automatic capture detection, a procedure that typically occurs on a beat-by-beat basis during pacing. Automatic capture detection verifies that a delivered pace pulse results in a captured response. When a captured response is not detected following a pace pulse, the pacemaker may deliver a back up safety pace to ensure consistent pacing. The back up pace may be delivered, for example, about 70-80 ms after the initial pace pulse. If a predetermined number of pace pulses delivered during normal pacing do not produce a captured response, the pacemaker may initiate a capture threshold test to determine the capture threshold. Alternatively, if a predetermined number of pacing pulses do not produce a captured response, the pacemaker may adjust the pacing energy for the next pacing pulse.

In accordance with various aspects of the invention, a cardiac signal following a pacing pulse is sensed. The sensed cardiac signal may be used to determine the cardiac response to the pacing pulse. Capture may be detected by comparing one or more characteristic features or samples of the cardiac signal following pacing to a reference or template representative of a captured response. If the one or more signal features or samples are consistent with the template or reference value, capture is detected. For example, capture may be detected by comparing a peak value, e.g., a positive or negative peak value, of the signal sensed after delivery of the pacing pulse to a peak threshold representative of a captured response. If the absolute value of the signal peak meets or exceeds the captured peak threshold, capture is detected. Similarly, non-capture may be detected by comparing a positive or negative peak value of the signal sensed after delivery of the pacing pulse to a peak threshold representative of a non-captured response. If the absolute value of the signal peak remains below the non-captured peak threshold, non-capture is detected.

In some circumstances, multiple features or samples of the cardiac signal may be compared to a template for cardiac response determination. A cardiac signal may be considered to be consistent with a template if the features, samples, or morphological characteristics of the cardiac signal are determined to be sufficiently similar to the template features, samples, or morphological characteristics. If a cardiac signal is sufficiently similar to a template representative of a particular type of cardiac response, then the cardiac signal may be classified as that particular type of cardiac response.

The graph of FIG. 1 illustrates signals indicative of captured and non-captured responses to pacing. Pacing pulses 110, 120 may be delivered to an atrial or ventricular heart chamber. The cardiac signal 112 sensed in the heart chamber following the first pacing pulse 110 is a captured response, having a peak amplitude 115 and peak timing 118. The cardiac signal 122 sensed following the second pacing pulse 120 is a non-captured response having a peak amplitude 125 and peak timing 128. The captured response 112 exhibits a relatively larger peak amplitude 115 than the peak amplitude 125 of the non-captured response. The relatively larger peak amplitude of the captured response signal can be used to discriminate between capture and non-capture. The timing 118, 128 of the peak amplitude of the captured or non-captured responses may be used along with the peak amplitude information to detect capture and/or non-capture.

Variability between patients, variability of device implantation configurations, and changes in patient conditions create significant issues for the creation and maintenance of templates and baseline references used for determining cardiac pacing responses. Further, templates or thresholds used for capture detection may be corrupted by the inclusion of noise, fusion beats or non-captured beats with intrinsic activity in a captured response template, for example. Embodiments of the present invention use median filtering methodologies to reduce spurious cardiac signals contributing to inaccuracies in captured response templates.

Figure 2:
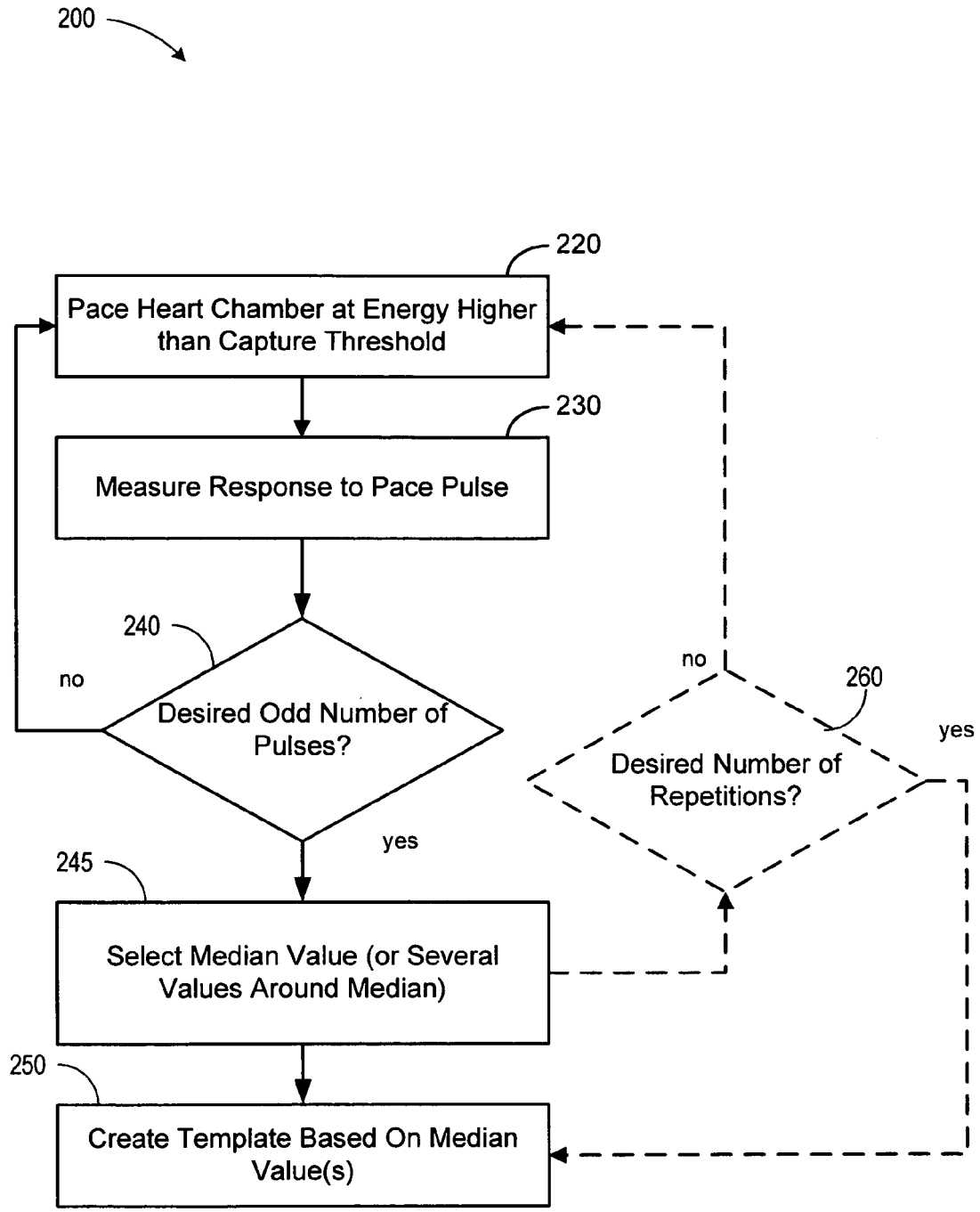
FIG. 2 is a flow chart of a method of initializing a capture template in accordance with embodiments of the present invention.

FIG. 2 is a flow chart of a method 200 of initializing a template in accordance with embodiments of the present invention. In an exemplary embodiment, a heart chamber is paced 220 at a rate higher than the intrinsic rate, and at a level higher than the capture threshold. Jittering the pacing rate by varying the pacing rate slightly and/or randomly for each beat may be additionally or alternatively used for avoiding fusion.

An odd number of pace pulses 240 are used, and the evoked response 230 is measured after each pace 220. For example, the captured response peak amplitude and peak amplitude timing may be measured for each captured response 230. The median value is then selected 245 for use in template creation 250. This process may be repeated 260, and median values for each repetition 260 may be averaged, to further reduce noise affecting the template. Alternately or additionally, several values around the median may be selected 245 for a larger odd number of pace pulses, and used for averaging.

In order to increase the likelihood that fusion beats are avoided in the template creation 250, an odd number, e.g., 33, is selected for the repetition 240 count. Pacing 220 and response measurement 230 are repeated 33 times, and each time the values of the peak response amplitude and peak timing within a response interval are recorded by the CRM device. All the peak response amplitudes and peak timing values are then ranked in ascending or descending order respectively. The median ranked value, in this case the value having a ranking of 17, is then selected as the template value for an evoked response. In an alternate example, the median ranked value, having a ranking of 17, and the 4 values surrounding the median, in this case values having rankings 13-16 and 18-21, may be averaged to provide the evoked response template value.

In still a further embodiment, pacing 220 and response measurement 230 are repeated 9 times, and each time the values of the peak response amplitude and peak timing within a response interval are recorded by the CRM device. All the peak response amplitudes and peak timing values are then ranked in ascending or descending order respectively. The median ranked value, in this case the value having a ranking of 5, is then selected as the first candidate template value for an evoked response template statistical analysis. The pacing 220 and response measurement 230 are repeated 9 more times, values ranked, and the value having a ranking of 5 is selected again, this time as the second candidate template value. This process may be repeated 260 for any desired repetitions of captured response analysis, until it is determined that the captured response candidate value(s) are representative of a true evoked response. The determination may be made after averaging a sufficient number of candidate values, after convergence is determined, or using other appropriate statistical principals.

Figure 3:
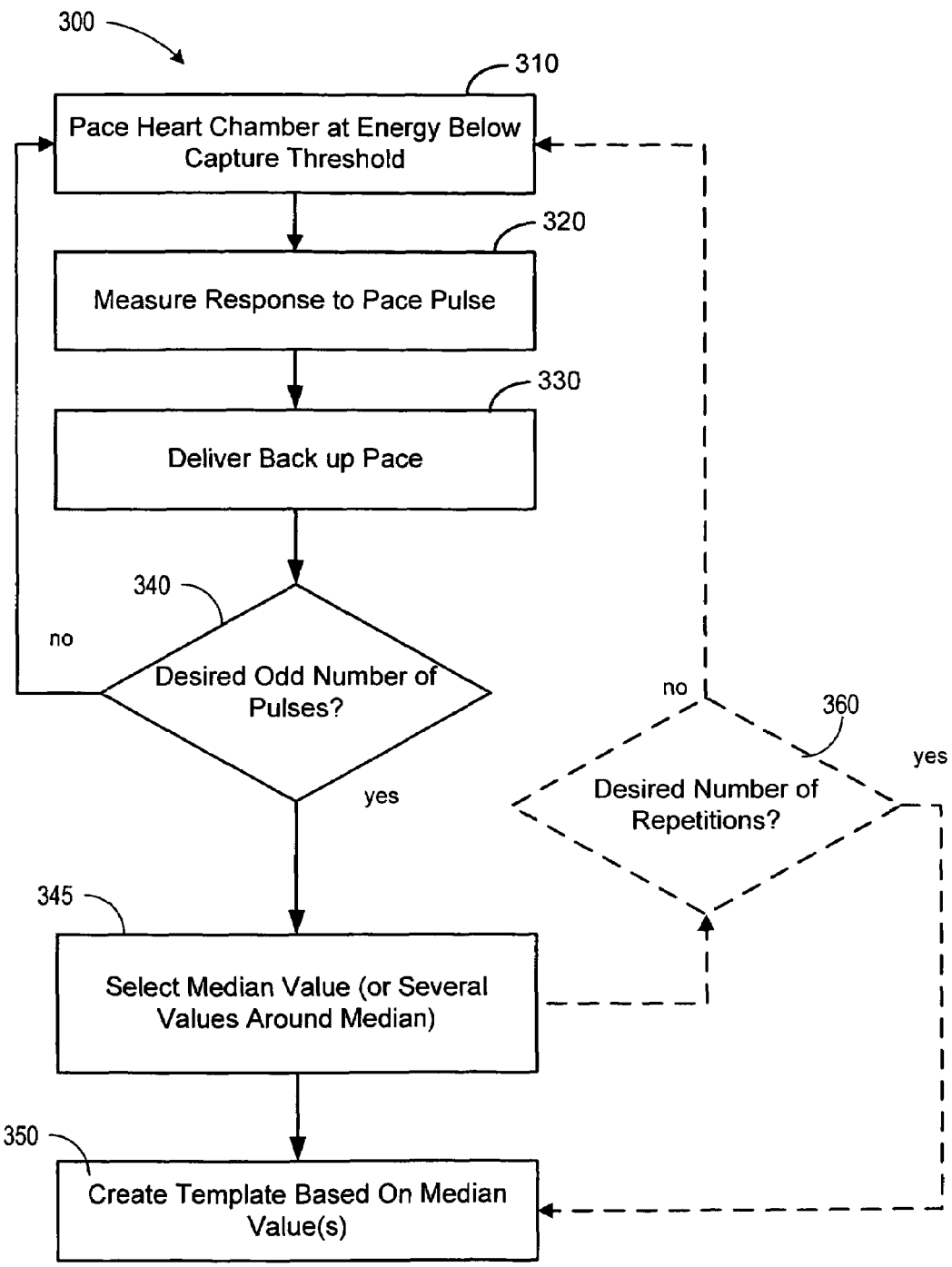
FIG. 3 is a flow chart of a method of initializing a non-capture template in accordance with embodiments of the present invention.

FIG. 2 is a flow chart of a method 200 of initializing a captured response template in accordance with embodiments of the present invention. Other types of cardiac response templates may also be created, updated, and/or refined using median filtering methodologies in accordance with the present invention. For example, as illustrated in FIG. 3, a non-captured response template may be formed using the methodologies of the present invention. As illustrated in FIG. 3, the heart may be paced 310 at a rate higher than the intrinsic rate, but at an energy level lower than the capture threshold. Jittering the pacing rate by varying the pacing rate slightly and/or randomly for each beat may be additionally or alternatively used for avoiding fusion.

Features of the cardiac signal following and associated with the pacing pulse are measured 320. For example, the peak amplitude and/or peak timing of the signal following the low level paces may be measured 320. Because pacing pulses delivered below the capture threshold will not produce capture, a back up pace may be delivered 330 after each primary pace 310 to ensure continuous pacing therapy delivery to the patient. The back up pace may be delivered 330 about 80 ms to about 100 ms following delivery of the primary pacing pulse.

An odd number of pacing pulses are delivered 340 and the system determines median values 345 of the measured amplitude, peak timing, or other measured feature value of the cardiac signals following the low level paces 310. The median values of the peak amplitude and/or peak timing measurements are selected 345 to create 350 a non-captured response template. The number of low level paces used to form the template is preferably an odd number 340. The larger the odd number 340 of paces, the greater the chance of avoiding fusion beats.

The process of delivering a pacing pulse, measuring feature values and determining a median value of the measured feature value may be repeated 360, and the median values for each repetition 360 may be averaged, to further reduce noise affecting the template. Alternately or additionally, several values around the median may be selected 345, and used for averaging.

Combinations of the methodologies exemplified in FIGS. 2-3 may also be used in accordance with the present invention. For example, a cardiac response to pacing may involve the utilization of one or both a non-captured response template and a captured response template to determine the cardiac pacing response. Median template creation methodologies in accordance with the present invention may also be useful for fusion detection and/or management. For example, if a cardiac signal sensed following pacing is inconsistent with a non-captured response template and a captured response template, the cardiac pacing response may be classified as a fusion or and unknown (possibly noise) response triggering a fusion/noise management process. Median filtering methodologies for cardiac response template generation in accordance with the present invention may also utilize adaptive baselines for threshold measurements as described in more detail below.

For purposes herein, the use of an odd number of pace pulses to find a median value shall be equivalent to providing an even number of pulses and disregarding or eliminating one or more pulses to arrive at an odd number, in order to define a median. Further, determining a median value shall be equivalent to ranking or ordering an odd or even number of responses and disregarding or eliminating a number of responses at the top and/or bottom of the rankings, effectively arriving at the approximation of a median or grouping around a median in accordance with the present invention.

Median template creation methodologies in accordance with the present invention may be used for both atrial and ventricular capture verification. Embodiments of the present invention may be useful with pacing pulses delivered to any heart chamber. For example, the pacing stimulation may be delivered to one or more of the right ventricle, the left ventricle, the right atrium, and the left atrium. Various embodiments of the invention involve using the same electrode combination for pacing and sensing. Other embodiments involve using an electrode combination for pacing that is different from the electrode combination used to sense the cardiac signal following pacing.

Variability between patients, variability of device implantation configurations, and changes in patient conditions create significant issues for both the creation and maintenance of templates and for capture verification. In order to detect captured response reliably, wide-band amplifiers may be used for cardiac response detection circuits. Baselines for such wide-band amplifiers often fluctuate beat-to-beat, especially when the pacing rate is high. Fluctuation at high pacing rates may be at least partly due to larger T-waves that occur relatively later than with lower pacing rates. The wide-band amplifier retains some of the T-wave spectrum, contributing to the fluctuation. This fluctuation may lead to false detection of capture or loss of capture.

Fluctuation of the cardiac signal baseline may lead to errors in peak amplitude measurement. Fluctuation of the baseline may be problematic in atrial and/or ventricular evoked response detection when the pacing rate is high. Fluctuation of baselines is also problematic in some evoked response sensing configurations, for example, when a ventricle is paced and an A-ring to V-tip electrode configuration is used for sensing. Using an adaptive baseline in accordance with embodiments of the present invention provides improved captured response detection. An adaptive baseline may be used beat-by-beat, to reduce errors in captured response detection due to these fluctuations. Further, an adaptive baseline may be combined with the median filtering approach for template initialization described herein.

Figure 4:
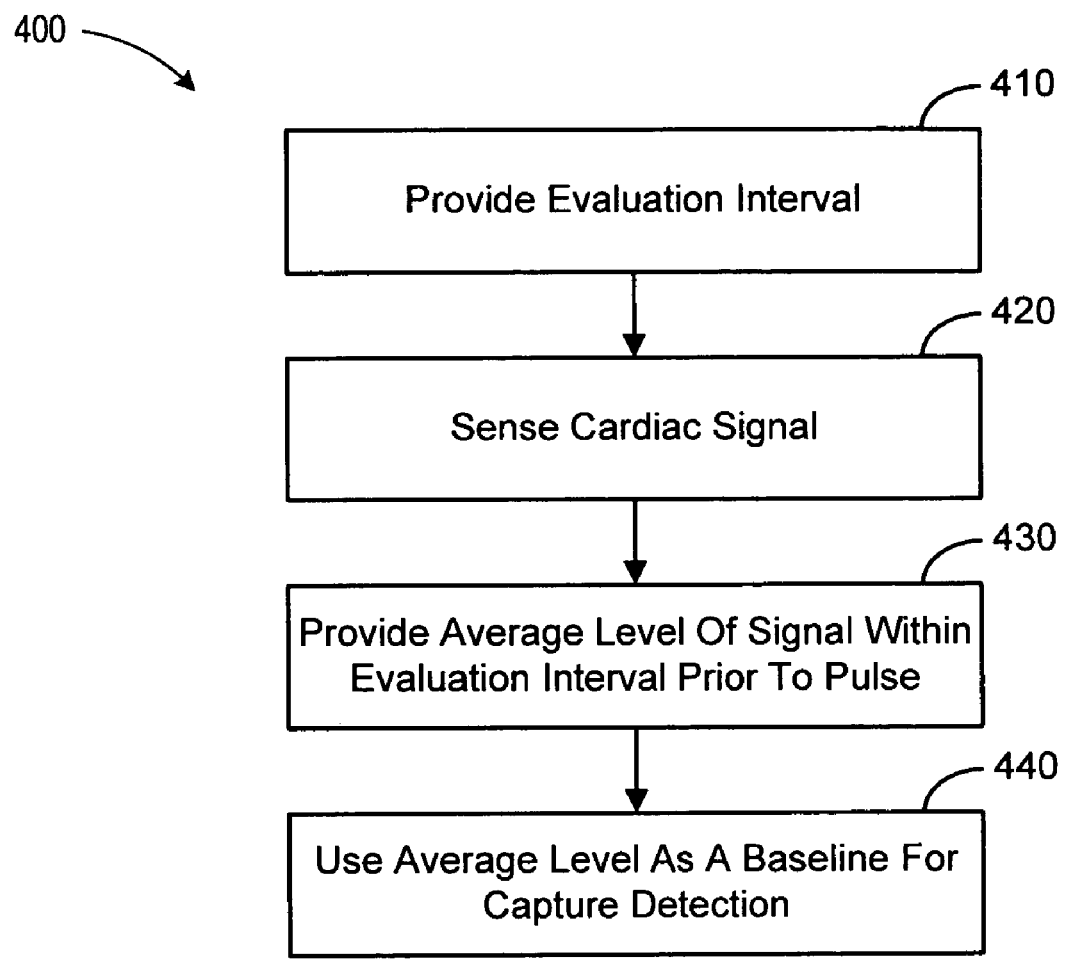
FIG. 4 is a flow chart of a method of adapting a baseline in accordance with embodiments of the present invention.

FIG. 4 is a flowchart of a method 400 of adapting a baseline in accordance with embodiments of the present invention. The method 400 measures 420 the cardiac signal during a moving evaluation interval 410 prior to the pacing pulse. The cardiac signal measured 420 during the moving interval is averaged 430 and the average value is used as a baseline 440 for the cardiac signal sensed following the pacing pulse. For example, a 3 to 5 millisecond interval 410 (and possibly up to 10 milliseconds or more) may be used as a moving interval 410. The cardiac signal 420 may, for example, be continuously evaluated for the average signal level 430 within the moving evaluation interval 410. The average signal level 430 may be determined by, for example, numerical averaging of digitized signals, using a low-pass filter and voltage hold circuit, or other filtering methodologies. The adaptive baseline serves as a reference point for measuring the cardiac signal peak sensed following delivery of the pacing pulse and used for detection of capture.

The adaptive baseline is particularly useful if a wideband amplifier is used for sensing cardiac signals used for cardiac response classification. In this scenario, the variation of the reference point for evoked response detection may vary significantly beat to beat, making an adaptive baseline for each beat desired. For example, in atrial pacing, for example, using the A-ring to V-tip sensing vector, the atrial pace can start before the signal (T-wave) returns to the nominal value. The residual signal from the T-wave may affect the evoked response detection. The adaptive baseline allows for higher pacing rates, for example, in atrial pacing.

The embodiments of the present system illustrated herein are generally described as being implemented in a cardiac rhythm management (CRM) device, such as an implantable pacemaker, that may operate in numerous pacing modes known in the art. The methods of the present invention may also be implemented in a variety of implantable or patient-external cardiac rhythm management devices, including single and multi chamber pacemakers, defibrillators, cardioverters, bi-ventricular pacemakers, cardiac resynchronizers, and cardiac monitoring systems, for example.

Although the present system is described in conjunction with an implantable cardiac defibrillator having a microprocessor-based architecture, it will be understood that the implantable cardiac defibrillator (or other device) may be implemented in any logic-based integrated circuit architecture, if desired.

Figure 5:
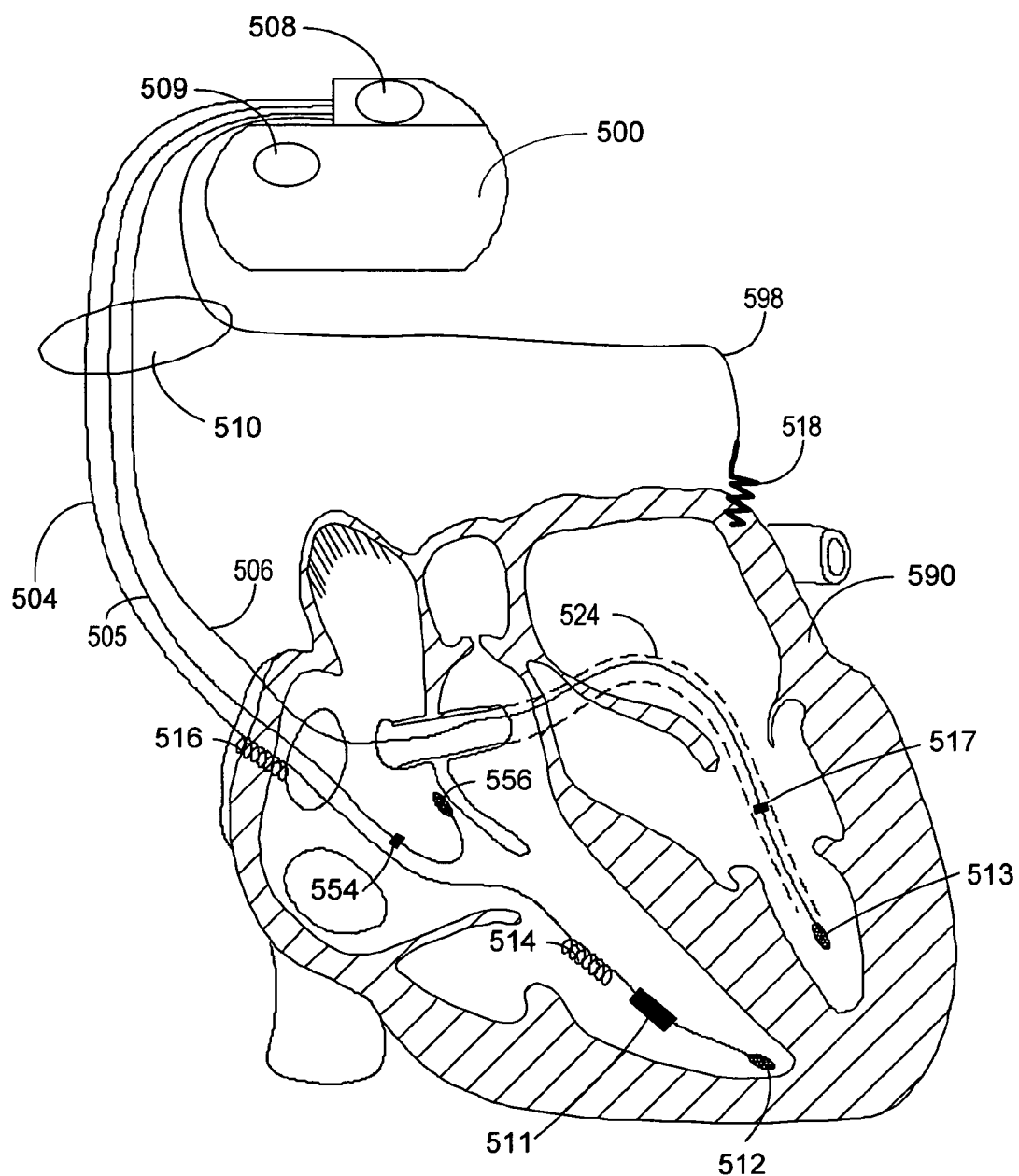
FIG. 5 illustrates implantable medical devices that may be used in connection with initialization of evoked response detection methodologies and adaptation of baselines for evoked response detection in accordance with embodiments of the invention.

Referring now to FIG. 5 of the drawings, there is shown a cardiac rhythm management system that may be used to initialize and adapt baselines and/or templates for evoked response detection in accordance with the present invention. The cardiac rhythm management system in FIG. 5 includes a cardiac rhythm management (CRM) device 500 electrically and physically coupled to a lead system 510. The housing and/or header of the CRM device 500 may incorporate one or more electrodes 508, 509 used to provide electrical stimulation energy to the heart and to sense cardiac electrical activity. The CRM device 500 may utilize all or a portion of the CRM device housing as a can electrode 509. The CRM device 500 may include an indifferent electrode 508 positioned, for example, on the header or the housing of the CRM device 500. If the CRM device 500 includes both a can electrode 509 and an indifferent electrode 508, the electrodes 508, 509 typically are electrically isolated from each other.

The lead system 510 is used to detect electric cardiac signals produced by the heart 590 and to provide electrical energy to the heart 590 under certain predetermined conditions to treat cardiac arrhythmias. The lead system 510 may include one or more electrodes used for pacing, sensing, and/or defibrillation. In the embodiment shown in FIG. 5, the lead system 510 includes an intracardiac right ventricular (RV) lead system 504, an intracardiac right atrial (RA) lead system 505, an intracardiac left ventricular (LV) lead system 506, and an extracardiac left atrial (LA) lead system 598. The lead system 510 of FIG. 5 illustrates one embodiment that may be used in connection with the atrial capture verification methodologies described herein. Other leads and/or electrodes may additionally or alternatively be used.

The lead system 510 may include intracardiac leads 504, 505, 506 implanted in a human body with portions of the intracardiac leads 504, 505, 506 inserted into a heart 590. The intracardiac leads 504, 505, 506 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 5, the lead system 510 may include one or more extracardiac leads 598 having electrodes, e.g., epicardial electrodes, positioned at locations outside the heart for sensing and/or pacing one or more heart chambers.

The right ventricular lead system 504 illustrated in FIG. 5 includes an SVC-coil 516, an RV-coil 514, an RV-ring electrode 511, and an RV-tip electrode 512. The right ventricular lead system 504 extends through the right atrium and into the right ventricle. In particular, the RV-tip electrode 512, RV-ring electrode 511, and RV-coil electrode 514 are positioned at appropriate locations within the right ventricle for sensing and delivering electrical stimulation pulses to the heart. The SVC-coil 516 is positioned at an appropriate location within the right atrium chamber of the heart 590 or a major vein leading to the right atrial chamber of the heart 590.

In one configuration, the RV-tip electrode 512 referenced to the can electrode 509 may be used to implement unipolar pacing and/or sensing in the right ventricle. Bipolar pacing and/or sensing in the right ventricle may be implemented using the RV-tip 512 and RV-ring 511 electrodes. In yet another configuration, the RV-ring 511 electrode may optionally be omitted, and bipolar pacing and/or sensing may be accomplished using the RV-tip electrode 512 and the RV-coil 514, for example. The right ventricular lead system 504 may be configured as an integrated bipolar pace/shock lead. The RV-coil 514 and the SVC-coil 516 are defibrillation electrodes.

The left ventricular lead 506 includes an LV distal electrode 513 and an LV proximal electrode 517 located at appropriate locations in or about the left ventricle for pacing and/or sensing the left ventricle. The left ventricular lead 506 may be guided into the right atrium of the heart via the superior vena cava. From the right atrium, the left ventricular lead 506 may be deployed into the coronary sinus ostium, the opening of the coronary sinus. The lead 506 may be guided through the coronary sinus to a coronary vein 524 of the left ventricle. This vein is used as an access pathway for leads to reach the surfaces of the left ventricle that are not directly accessible from the right side of the heart. Lead placement for the left ventricular lead 506 may be achieved via subclavian vein access and a preformed guiding catheter for positioning of the LV electrodes 513, 517 adjacent to the left ventricle.

Unipolar pacing and/or sensing in the left ventricle may be implemented, for example, using the LV distal electrode 513 referenced to the can electrode 509. The LV distal electrode 513 and the LV proximal electrode 517 may be used together as bipolar sense and/or pace electrodes for the left ventricle. The left ventricular lead 506 and the right ventricular lead 504, in conjunction with the CRM device 500, may be used to provide cardiac resynchronization therapy such that the ventricles of the heart are paced substantially simultaneously, or in phased sequence, to provide enhanced cardiac pumping efficiency for patients suffering from chronic heart failure.

The right atrial lead 505 includes a RA-tip electrode 556 and an RA-ring electrode 554 positioned at appropriate locations in the right atrium for sensing and pacing the right atrium. In one configuration, the RA-tip 556 referenced to the can electrode 509, for example, may be used to provide unipolar pacing and/or sensing in the right atrium. In another configuration, the RA-tip electrode 556 and the RA-ring electrode 554 may be used to effect bipolar pacing and/or sensing.

FIG. 5 illustrates one embodiment of a left atrial lead system 598. In this example, the left atrial lead 598 is implemented as an extracardiac lead with an LA distal electrode 518 positioned at an appropriate location outside the heart 590 for sensing and pacing the left atrium. Unipolar pacing and/or sensing of the left atrium may be accomplished, for example, using the LA distal electrode 518 to the can 509 pacing vector. The left atrial lead 598 may be provided with additional electrodes used to implement bipolar pacing and/or sensing of the left atrium.

Figure 6:
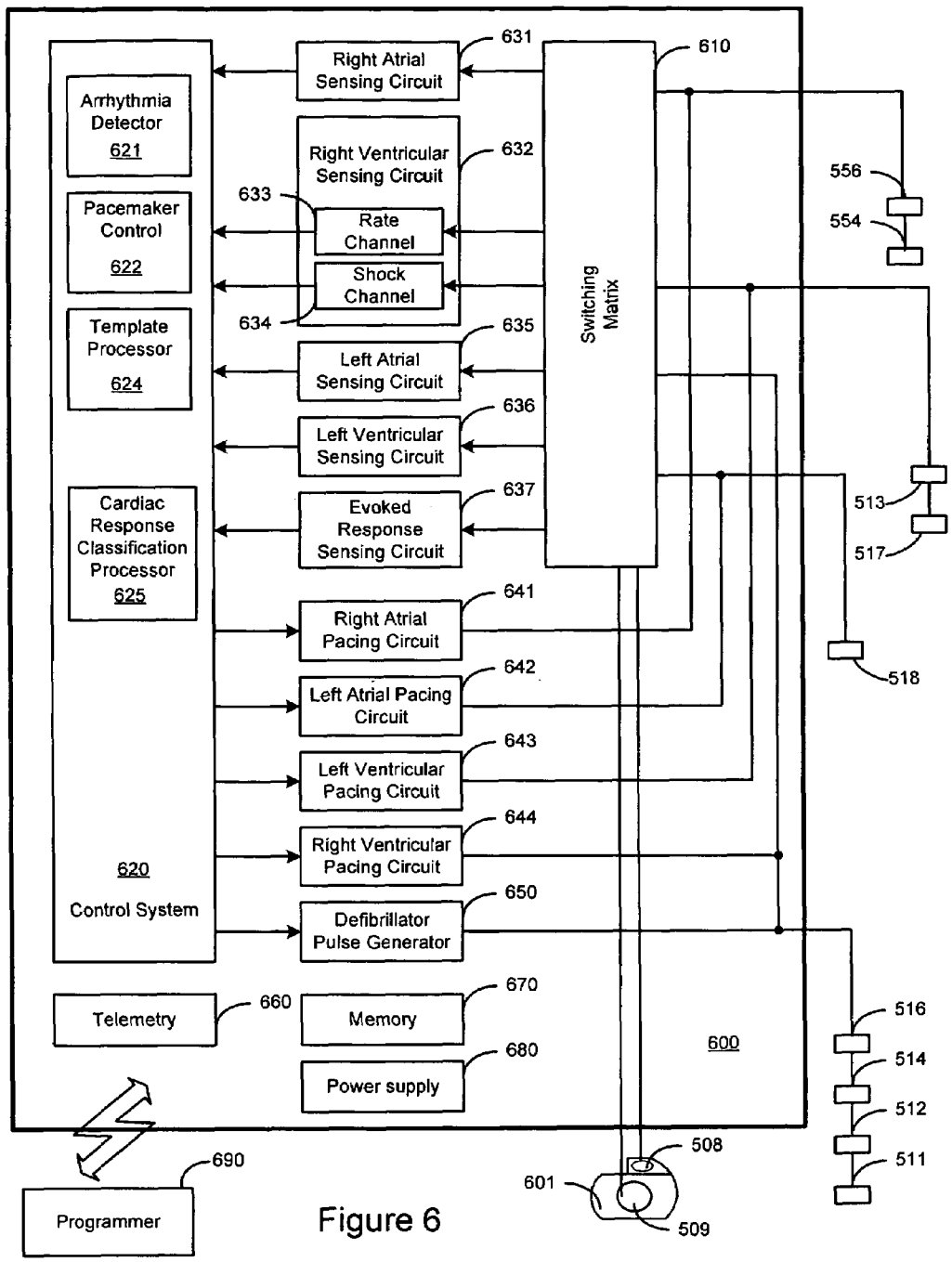
FIG. 6 is a block diagram of an implantable medical device that may be used to initialize evoked response detection and/or adapt baselines for evoked response detection in accordance with embodiments of the invention.

Referring now to FIG. 6, there is shown an embodiment of a cardiac pacemaker/defibrillator 600 suitable for implementing adaptable baselines for evoked response detection and initialization of templates for evoked response detection in accordance with embodiments of the invention. FIG. 6 shows a cardiac rhythm management device exemplified as a pacemaker/defibrillator divided into functional blocks. It is understood by those skilled in the art that there exist many possible configurations in which these functional blocks can be arranged. The example depicted in FIG. 6 is one possible functional arrangement. Other arrangements are also possible. For example, more, fewer or different functional blocks may be used to describe a cardiac pacemaker/defibrillator suitable for implementing the atrial capture verification methodology of the present invention. In addition, although the cardiac pacemaker/defibrillator 600 depicted in FIG. 6 contemplates the use of a programmable microprocessor-based logic circuit, other circuit implementations may be utilized.

The cardiac pacemaker/defibrillator 600 depicted in FIG. 6 includes circuitry for receiving cardiac signals from a heart and delivering electrical stimulation energy to the heart in the form of pacing pulses or defibrillation shocks. In one embodiment, the circuitry of the cardiac pacemaker/defibrillator 600 is encased and hermetically sealed in a housing 601 suitable for implanting in a human body. Power to the cardiac pacemaker/defibrillator 600 is supplied by an electrochemical battery 680. A connector block (not shown) is attached to the housing 601 of the cardiac pacemaker/defibrillator 600 to allow for the physical and electrical attachment of the lead system conductors to the circuitry of the cardiac pacemaker/defibrillator 600.

The cardiac pacemaker/defibrillator 600 may be a programmable microprocessor-based system, including a control system 620 and a memory 670. The memory 670 may store parameters for various pacing, defibrillation, and sensing modes, along with other parameters. Further, the memory 670 may store data indicative of cardiac signals received by other components of the cardiac pacemaker/defibrillator 600. The memory 670 may be used, for example, for storing historical EGM and therapy data. The historical data storage may include, for example, data obtained from long term patient monitoring used for trending or other diagnostic purposes. Historical data, as well as other information, may be transmitted to an external programmer unit 690 as needed or desired.

The control system 620 and memory 670 may cooperate with other components of the cardiac pacemaker/defibrillator 600 to control the operations of the cardiac pacemaker/defibrillator 600. The control system depicted in FIG. 6 incorporates a cardiac response classification processor 625 for classifying cardiac responses to pacing stimulation in accordance with various embodiments of the present invention. The control system 620 may include additional functional components including a pacemaker control circuit 622, an arrhythmia detector 621, and a template processor 624, along with other components for controlling the operations of the cardiac pacemaker/defibrillator 600.

Telemetry circuitry 660 may be implemented to provide communications between the cardiac pacemaker/defibrillator 600 and an external programmer unit 690. In one embodiment, the telemetry circuitry 660 and the programmer unit 690 communicate using a wire loop antenna and a radio frequency telemetric link, as is known in the art, to receive and transmit signals and data between the programmer unit 690 and the telemetry circuitry 660. In this manner, programming commands and other information may be transferred to the control system 620 of the cardiac pacemaker/defibrillator 600 from the programmer unit 690 during and after implant. In addition, stored cardiac data pertaining to capture threshold, capture detection and/or cardiac response classification, for example, along with other data, may be transferred to the programmer unit 690 from the cardiac pacemaker/defibrillator 600.

In the embodiment of the cardiac pacemaker/defibrillator 600 illustrated in FIG. 6, electrodes RA-tip 556, RA-ring 554, RV-tip 512, RV-ring 511, RV-coil 514, SVC-coil 516, LV distal electrode 513, LV proximal electrode 517, LA distal electrode 518, indifferent electrode 508, and can electrode 509 are coupled through a switch matrix 610 to sensing circuits 631-637.

A right atrial sensing circuit 631 serves to detect and amplify electrical signals from the right atrium of the heart. Unipolar sensing may be implemented, for example, by sensing voltages developed between the RA-tip 556 and the can electrode 509. Outputs from the right atrial sensing circuit are coupled to the control system 620.

A right ventricular sensing circuit 632 serves to detect and amplify electrical signals from the right ventricle of the heart. The right ventricular sensing circuit 632 may include, for example, a right ventricular rate channel 633 and a right ventricular shock channel 634. Right ventricular cardiac signals sensed through use of the RV-tip 512 electrode are right ventricular near-field signals and are denoted RV rate channel signals. A bipolar RV rate channel signal may be sensed as a voltage developed between the RV-tip 512 and the RV-ring 511. Alternatively, bipolar sensing in the right ventricle may be implemented using the RV-tip electrode 512 and the RV-coil 514. Unipolar rate channel sensing in the right ventricle may be implemented, for example, by sensing voltages developed between the RV-tip 512 and the can electrode 509.

Right ventricular cardiac signals sensed through use of the RV-coil electrode 514 are far-field signals, also referred to as RV morphology or RV shock channel signals. More particularly, a right ventricular shock channel signal may be detected as a voltage developed between the RV-coil 514 and the SVC-coil 516. A right ventricular shock channel signal may also be detected as a voltage developed between the RV-coil 514 and the can electrode 509. In another configuration the can electrode 509 and the SVC-coil electrode 516 may be electrically shorted and a RV shock channel signal may be detected as the voltage developed between the RV-coil 514 and the can electrode 509/SVC-coil 516 combination.

Outputs from the right ventricular sensing circuit 632 are coupled to the control system 620. In one embodiment of the invention, rate channel signals and shock channel signals may be used to develop morphology templates for analyzing cardiac signals. In this embodiment, rate channel signals and shock channel signals may be transferred from the right ventricular sensing circuit 632 to the control system 620 and to a template processor 624 where the morphological characteristics of a cardiac signal are analyzed. The template processor 624 works in combination with the control system 620 and the memory 670 to generate and maintain various types of templates, including, for example, templates used for arrhythmia discrimination as well as cardiac response classification as described in more detail herein.

Left atrial cardiac signals may be sensed through the use of one or more left atrial electrodes 515, 518, which may be configured as epicardial electrodes. A left atrial sensing circuit 635 serves to detect and amplify electrical signals from the left atrium of the heart. Bipolar sensing and/or pacing in the left atrium may be implemented, for example, using the LA distal electrode 518 and the LA proximal electrode 515. Unipolar sensing and/or pacing of the left atrium may be accomplished, for example, using the vector from the LA distal electrode 518 to the can electrode 509 or the LA proximal electrode 515 to the can electrode 509.

A left ventricular sensing circuit 636 serves to detect and amplify electrical signals from the left ventricle of the heart. Bipolar sensing in the left ventricle may be implemented, for example, by sensing voltages developed between the LV distal electrode 513 and the LV proximal electrode 517. Unipolar sensing may be implemented, for example, by sensing voltages developed between the LV distal electrode 513 or the LV proximal electrode 517 to the can electrode 509.

Optionally, an LV coil electrode (not shown) may be inserted into the patient's cardiac vasculature, e.g., the coronary sinus, adjacent to the left heart. Signals detected using combinations of the LV electrodes, 513, 517, LV coil electrode (not shown), and/or can electrodes 509 may be sensed and amplified by the left ventricular sensing circuitry 636. The output of the left ventricular sensing circuit 636 is coupled to the control system 620.

The outputs of the switching matrix 610 may be operated to couple selected combinations of electrodes 511, 512, 513, 514, 516, 517, 518, 554, and 556 to an evoked response sensing circuit 637. The evoked response sensing circuit 637 serves to sense and amplify voltages developed using various combinations of electrodes for cardiac response classification in accordance with embodiments of the invention.

In the embodiments described below, various combinations of pacing and sensing electrodes may be utilized in connection with pacing and sensing the cardiac signal following the pace pulse to classify the cardiac response to the pacing pulse. For example, in some embodiments, a first electrode combination is used for pacing a heart chamber and a second electrode combination is used to sense the cardiac signal following pacing. In other embodiments, the same electrode combination is used for pacing and sensing.

Sensing the cardiac signal following a pacing pulse using the same electrode combination for both pacing and sensing may yield a sensed cardiac signal including a pacing artifact component associated with residual post pace polarization at the electrode-tissue interface. The pacing artifact component may be superimposed on a smaller signal indicative of the cardiac response to the pacing pulse, i.e., the evoked response. The pacing output circuitry may include a coupling capacitor to block DC components from the heart and to condition the pacing stimulus pulse. A relatively large coupling capacitor may cause a larger pacing artifact that decays exponentially over a relatively long period of time.

The pacemaker control circuit 622, in combination with pacing circuitry for the left atrium, right atrium, left ventricle, and right ventricle may be implemented to selectively generate and deliver pacing pulses to the heart using various electrode combinations. The pacing electrode combinations may be used to effect bipolar or unipolar pacing of the heart chambers as described above.

As described above, bipolar or unipolar pacing pulses may be delivered to a heart chamber using one of the pacing vectors as described above. The electrical signal following the delivery of the pacing pulses may be sensed through various sensing vectors coupled through the switch matrix 610 to the evoked response sensing circuit 637 and used to classify the cardiac response to pacing.

In one example, the cardiac signal following the pacing pulse may be sensed using the same vector as was used for delivery of the pacing pulse. An adaptable cardiac response classification interval may be defined following the pacing pulse and used to classify the cardiac response to pacing. The adaptable cardiac response classification interval may be used to classify the cardiac response to pacing as one of a captured response, a non-captured response, and a fusion beat, for example.

Subcutaneous electrodes may provide additional sensing vectors useable for cardiac response classification. In one implementation, a cardiac rhythm management system may involve a hybrid system including a first device, e.g. a pacemaker coupled to an intracardiac lead system, configured to pace the heart, and a second device, e.g. a pacemaker/defibrillator coupled to a subcutaneous lead system, configured to perform functions other than pacing. The second device may be employed to detect and classify cardiac responses to pacing based on signals sensed using subcutaneous electrode arrays. The first and second devices may operate cooperatively with communication between the devices occurring over a wireless link, for example. Examples of subcutaneous electrode systems and devices are described in commonly owned U.S. patent applications Ser. No. 10/462,001, filed Jun. 13, 2003, now U.S. Publication No. 20040230229, and 10/465,520, filed Jun. 19, 2003, now U.S. Publication No. 20040230230, which are incorporated herein by reference in their respective entireties.

For right ventricular pacing, bipolar pacing may be delivered using the RV-tip electrode 512 and the RV-ring electrode 511. Unipolar pacing may be delivered using the RV-tip 512 to can electrode 509 vector. Sensing electrode combinations for cardiac response classification following RV pacing include RV-coil 514 to SVC-coil 516 tied to the can electrode 509, RV-coil 514 to can electrode 509, and, if the system includes a left ventricular lead, LV distal electrode 513 to LV proximal electrode 517.

In an example of left ventricular pacing, bipolar pacing pulses may be delivered to the left ventricle between the LV distal electrode 513 and the LV proximal electrode 517. In another example, unipolar pacing pulses may be delivered to the left ventricle, for example, between the LV distal electrode 513 and the can electrode 509. The cardiac signal following the delivery of the pacing pulses may be sensed using the LV proximal electrode 517 and the can electrode 509.

In an example of right atrial pacing, bipolar pacing pulses may be delivered to the right atrium between the RA-tip electrode 556 and the RA-ring electrode 554. In another example, unipolar pacing pulses may be delivered to the right atrium, for example, between the RA-tip electrode 556 and the can electrode 509. For unipolar right atrial pacing, an electrode combination useful for sensing cardiac signals following pacing for cardiac response classification includes the RA-ring 554 to indifferent electrode.

In an example of left atrial pacing, bipolar pacing pulses may be delivered to the left atrium between the LA distal electrode 518 and an LA proximal electrode (not shown). In another example, unipolar pacing pulses may be delivered to the left atrium, for example, between the LA distal electrode 518 and the can electrode 509. The cardiac signal following the delivery of the pacing pulses and used for atrial capture verification may be sensed using the RA-tip 556 to RA-ring 554 vector.

In one embodiment of the invention, a switching matrix 610 is coupled to the RA-tip 556, RA-ring 554, RV-tip 512, RV-coil 514, LV distal electrode 513, LV proximal electrode 517, SVC coil 516, LA distal electrode 518, LA proximal electrode 515, indifferent 508, and can electrode 509. The switching matrix 610 may be arranged to provide connections to various configurations of pacing and defibrillation electrodes. The outputs of the switching matrix 610 are coupled to an evoked response (ER) sensing circuit 637 that serves to sense and amplify cardiac signals detected between the selected combinations of electrodes. The detected signals are coupled through the ER amplifier 637 to a cardiac response classification processor 625. The cardiac response classification processor 625 includes circuitry configured to adapt a cardiac response classification interval and to classify the cardiac response to a pacing stimulation, including, for example, classifying captured responses, non-captured responses, and fusion responses, in accordance with embodiments of the invention.

Various methods and systems for establishing and adapting templates useful for capture threshold testing and capture verification, aspects of which may be utilized in connection with implementing cardiac response detection according to embodiments of the invention, are described in commonly owned U.S. patent application Ser. No. 10/448,260, filed May 28, 2003, now U.S. Publication No. 20040243014, which is incorporated herein by reference.

A number of the examples presented herein involve block diagrams illustrating functional blocks used for coordinated monitoring, diagnosis and/or therapy functions in accordance with embodiments of the present invention. It will be understood by those skilled in the art that there exist many possible configurations in which these functional blocks can be arranged and implemented. The examples depicted herein provide examples of possible functional arrangements used to implement the approaches of the invention.

It is understood that the components and functionality depicted in the figures and described herein can be implemented in hardware, software, or a combination of hardware and software. It is further understood that the components and functionality depicted as separate or discrete blocks/elements in the figures in general can be implemented in combination with other components and functionality, and that the depiction of such components and functionality in individual or integral form is for purposes of clarity of explanation, and not of limitation.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of adapting a baseline for characterizing a cardiac response to pacing, comprising:

delivering a pacing pulse to a heart chamber;

sensing a cardiac signal associated with the pacing pulse;

establishing a baseline amplitude of the cardiac signal using data acquired in a moving time interval prior to delivery of the pacing pulse;

measuring a peak amplitude of the cardiac signal referenced from the baseline amplitude; and using the peak amplitude referenced from the baseline amplitude to determine the cardiac response to the pacing pulse.

2. The method of claim 1, wherein the moving time interval has a range of about 3 msec to about 10 msec.

3. The method of claim 1, wherein establishing the baseline amplitude comprises averaging the data acquired during the time interval.

4. The method of claim 1, wherein establishing the baseline amplitude for the cardiac signal comprises establishing the baseline amplitude for each cardiac beat.

5. The method of claim 1, wherein delivering the pacing pulse to the heart chamber comprises delivering the pacing pulse to an atrium.

6. A medical system, comprising:
a pacing circuit configured to deliver a pacing pulse to a patient;
a sensing circuit configured to sense cardiac signals associated with the pacing pulse; and
a cardiac response processor coupled to the sensing circuit, the cardiac response processor configured to establish a baseline amplitude of a cardiac signal using data acquired in a time interval prior to the delivery of the pacing pulse, the cardiac response processor configured to measure a peak amplitude of the cardiac signal referenced from the baseline amplitude and use the peak amplitude referenced from the baseline amplitude to determine the cardiac response to the pacing pulse.

7. The system of claim 6, wherein the cardiac response processor is configured to average the data within the time interval.

8. The system of claim 6, wherein the cardiac response processor comprises a filter configured to filter the cardiac signal prior to establishing the baseline amplitude.

9. The system of claim 6, wherein the cardiac response processor comprises a voltage holder configured to maintain the baseline amplitude.

10. The system of claim 6, wherein the moving time interval has a range of about 3 msec to about 10 msec.

11. The system of claim 6, wherein the cardiac response processor is configured to establish the baseline amplitude for each paced beat.

12. The system of claim 6, wherein the pacing pulse comprises an atrial pacing pulse.

13. The system of claim 6, wherein the pacing pulse comprises a ventricular pacing pulse.

14. A cardiac device, comprising:
a pacing circuit configured to deliver a pacing pulse to a heart chamber;
a sensing circuit configured to sense a cardiac signal from the heart;
means for establishing a baseline amplitude of the cardiac signal using data acquired in a moving a time interval prior to the delivery of the pacing pulse; and
means for determining the cardiac response to the pacing pulse based on a peak amplitude of the cardiac signal associated with the pacing pulse referenced from the baseline amplitude.

15. The cardiac device of claim 14, further comprising means for averaging the data acquired in a moving time interval to establish the baseline amplitude.

* * * * *

UNITED STATES PATENT AND TRADEMARK OFFICE
CERTIFICATE OF CORRECTION

PATENT NO. : 7,330,761 B2 Page 1 of 1
APPLICATION NO. : 11/012608
DATED : February 12, 2008
INVENTOR(S) : Zhang It is certified that error appears in the above-identified patent and that said Letters Patent is hereby corrected as shown below:

Col. 1, line 7: "filed Dec. 15, 2004" should read --filed Dec. 15, 2004--.

Claim 14, line 2: "in a moving a time" should read --in a moving time--.

Signed and Sealed this

Eighth Day of July, 2008

JON W. DUDAS
*Director of the United States Patent and Trademark Office*

UNITED STATES PATENT AND TRADEMARK OFFICE
CERTIFICATE OF CORRECTION

PATENT NO. : 7,330,761 B2 Page 1 of 1
APPLICATION NO. : 11/012608
DATED : February 12, 2008
INVENTOR(S) : Zhang It is certified that error appears in the above-identified patent and that said Letters Patent is hereby corrected as shown below:

Col. 1, line 7: "filed Dec. 15, 2004" should read --filed Dec. 15, 2004--.

Col. 16, Claim 14, line 26: "in a moving a time" should read --in a moving time--.

This certificate supersedes the Certificate of Correction issued July 8, 2008.

Signed and Sealed this

Twenty-ninth Day of July, 2008

JON W. DUDAS
*Director of the United States Patent and Trademark Office*